United States Patent [19]
Haskill et al.

[11] Patent Number: 5,455,330
[45] Date of Patent: Oct. 3, 1995

[54] INTERLEUKIN-1 ANTAGONIST AND USES THEREOF

[75] Inventors: John S. Haskill, Chapel Hill, N.C.; George Martin, Berkeley; Peter Ralph, Orinda, both of Calif.

[73] Assignee: Cetus Oncology Corporation, Emeryville, Calif.

[21] Appl. No.: 85,455

[22] Filed: Jun. 30, 1993

Related U.S. Application Data

[63] Continuation of Ser. No. 877,274, Apr. 29, 1992, abandoned, which is a continuation of Ser. No. 517,276, May 1, 1990, abandoned.

[51] Int. Cl.$^6$ .......................... A61K 38/16; A61K 38/20; C07K 14/545; C07K 14/435
[52] U.S. Cl. .................. 530/350; 530/351; 435/69.1; 435/69.5; 435/69.52
[58] Field of Search ..................... 530/350, 351; 435/68.5, 69.52; 930/141

[56] References Cited

U.S. PATENT DOCUMENTS 5,075,222  12/1991  Hannum et al. ................. 435/69.1
5,359,032  10/1994  Dayer et al. ..................... 530/350

FOREIGN PATENT DOCUMENTS 8901946  3/1989  WIPO.
8911540  11/1989  WIPO.
9010068  9/1990  WIPO.

OTHER PUBLICATIONS

Hannum et al, *Nature* 343, 1990, pp. 336–346.
Eisenberg et al *Nature* 343/1990, pp. 341–346.
Fiorentino et al, *J Exp Med* 170, 1989, pp. 2081–2095.
Seckinger et al, *J Exp Med* 167, 1988, pp. 1511–1516.
Maliszewski et al, *J Immunol* 144, 1990, pp. 3028–3033.
Gosset et al, *Am Rev Respir Dis* 1988, pp. 40–46, vol. 138.
Oppenheim et al, *Immunal Today* 7(2) 1986, pp. 45–56.
Lotz et al, *Science* 241, 1988, pp. 1218–1221.
Fryling et al, *Cancer Res* 49, 1989, pp. 3333–3337.
Sugimura et al, *Eur J. Immunol* 1989, vol. 19, pp. 1357–1364.
Carter, D. B., et al., 1990, Nature, 344:633–638.
Hannum, C. H. et al., 1990, Nature, 343:336–346.
Eisenberg, S. P., et al., 1990, Nature, 343:341–346.

*Primary Examiner*—Marianne P. Allen
*Attorney, Agent, or Firm*—Thomas C. Meyers; Paul B. Savereide; Robert P. Blackburn

[57] ABSTRACT

Medicaments that have prophylactic or therapeutic applications for the treatment of disease resulting from the production of cytokines, particularly IL-1, that effectively inhibit the biological activity of the cytokines wherein the medicaments are characterized by being proteinaceous materials lacking a signal sequence for which a cDNA sequence has been identified and sequenced.

1 Claim, 2 Drawing Sheets

CA 2

3    CTGAGGACCAGCC.TTGAGGGGTGGACCCTCAGAAGGCGTCACAACAACC   51

52   TGGTCACA.GACTCTGCCTCCTCTTCAACTGACCAGCCTCCATGCTGCCT   100

101  CCAGAAT.GTCTTTCTAATGTGTGAATCAGAGCACAGCagGGGGTGCACA   149

150  AAGCCCTTCCATGtCGCCTCTgCATTCA.GGATCAAXCCCCGACCACCTg   198

199  CCCAACCTGCTC

FIG. 1

```
AGCTCCACCCTGGGAGGGACTGTGGCCCAGGTACTGCCCGGGTGCTACTT          -71

TATGGGCAGCAGCTCAGTTGAGTTAGAGTCTGGAAGACCTCAGA.AGACC          -22

MetAlaLeuGluThrIleCysArgPro
TCCTGTCCTATGAGGCCCTCCCCATGGCTTTAGAGACGATCTGCCGACCC           27
                                                             63
SerGlyArgLysSerSerLysMetGlnAlaPheArgIleTryAspValAs
TCTGGGAGAAAATCCAGCAAGATGCAAGCCTTCAGAATCTGGGATGTTAA           77 nGlnLysThrPheTyrLeuArgAsnAsnGlnLeuValAlaGlyTyrLeuG
CCAGAAGACCTTCTATCTGAGGAACAACCAACTAGTTGCTGGATACTTGC          127 lnGlyProAsnValAsnLeuGluGluLysIleAspValValProIleGlu
AAGGACCAAATGTCAATTTAGAAGAAAAGATAGATGTGGTACCCATTGAG          177

ProHisAlaLeuPheLeuGlyIleHisGlyGlyLysMetCysLeuSerCy
CCTCATGCTCTGTTCTTGGGAATCCATGGAGGGAAGATGTGCCTGTCCTG          227 sValLysSerGlyAspGluThrArgLeuGlnLeuGluAlaValAsnIleT
TGTCAAGTCTGGTGATGAGACCAGACTCCAGCTGGAGGCAGTTAACATCA          277 hrAspLeuSerGluAsnArgLysGlnAspLysArgPheAlaPheIleArg
CTGACCTGAGCGAGAACAGAAAGCAGGACAAGCGCTTCGCCTTCATCCGC          327

SerAspSerGlyProThrThrSerPheGluSerAlaAlaCysProGlyTr
TCAGACAGTGGCCCCACCACCAGTTTTGAGTCTGCCGCCTGCCCCGGTTG          377 pPheLeuCysThrAlaMetGluAlaAspGlnProValSerLeuThrAsnM
GTTCCTCTGCACAGCGATGGAAGCTGACCAGCCCGTCAGCCTCACCAATA          427 etProAspGluGlyValMetValThrLysPheTyrPheGlnGluAspGlu
TGCCTGACGAAGGCGTCATGGTCACCAAATTCTACTTCCAGGAGGACGAG          477

TAG                                                         480
```

FIG.2

INTERLEUKIN-1 ANTAGONIST AND USES THEREOF

This is a continuation of U.S. application Ser. No. 07/877,274, filed Apr. 29, 1992, now abandoned, which is a continuation of U.S. application Ser. No. 07/517,276, filed May 1, 1990, now abandoned.

FIELD OF THE INVENTION

This invention is in the field of molecular biology/biochemistry. Described herein are compositions that have prophylactic or therapeutic applications for the treatment of diseases resulting from the production of cytokines. More specifically, an inhibitory material is shown that effects the biological activity of the cytokine, interleukin- 1 (IL-1).

BACKGROUND OF THE INVENTION

Cytokines are small molecular weight proteins that have a myriad of biological functions. For example, cytokines are known to be capable of stimulating their own synthesis, as well as the production of other cytokines from a variety of cell types. They are also associated with disease. A good example is the presence of the cytokines interleukin-1 (IL-1 ) and tumor necrosis factor (TNF). IL-1 has been demonstrated to have multiple biological activities with the two prominent being fever production and lymphocyte activation. Moreover, both cytokines, alone or in combination, cause a shock state in animals that hemodynamically and hematologically is characteristic of septic shock in man caused by bacterial infection. TNF, in addition, has recently been shown to be involved in initiating the expression of human immunodeficiency virus in human cells that carry latent virus. Folks et al., 1989, *Proc,, Natl. Acad, Sci. USA,* 86:2365. TNF and IL-1 also play a role in various autoimmune diseases, particularly arthritis. Duff, et al., 1987, *International Conference on Tumor Necrosis Factor and Related Cytotoxins,* 175:10.

In addition to IL-1 and TNF, another cytokine, IL-6, has recently been shown to be involved in infection, particularly sepsis, as well as in affecting the growth of tumor cells. Hack, et al., 1989, *Blood,* 74:1704, and Miki fall, 1989, *FEB,* 250: 607. IL-6 is also termed hybfidoma growth factor, intefferon-beta-2, B-cell stimulatory factor 2, 26 kilodalton protein, and hepatocyte stimulating factor.

As alluded to above, IL-1 it is one of several cytokines produced and secreted by macrophages upon stimulation with bacterial endotoxins, particularly LPS, and thus is suspected of playing a role in causing the disease cascade following an organisms exposure to endotoxin. For example, one of the clinical symptoms of sepsis is intravascular coagulation which is reflected in decreased plasma concentrations of various coagulation factors, such as Factor XII. This aspect of the clinical course of the disease is consistent with in vitro studies which have shown that LPS can activate both the contact system of intrinsic coagulation, as well as the complement system. Morris, E. C., et al., 1974, *J. of Experimental Med.,* 140:797 and Morrison, D. C., et al., 1978, *American Journal of Pathology,* 93:527. IL-1 interaction with endothelial cells has been shown to enhance procoagulant activity and endothelial cell adhesiveness for leukocytes. Also as a consequence of endotoxin exposure, IL-1 is thought to induce an inhibitor of tissue plasminogen activator which would exasperate the coagulation events occurring during an acute inflammatory reactions. Finally, IL-1 is thought to cause the production of platelet activating factor and arachidonic acid metabolites, both of which are involved in an organism's response to endotoxin. It is worth noting that platelet activating factor and arachidonic acid metabolites are also directly produced in response to endotoxin.

There are two forms of IL-1:IL-1α and IL-1β. Although these molecules share limited sequence homology they have similar biological activity. Dinarello, C. A., et al., 1986, *Journal Clinical Invest.,* 77:1734. Both molecules have molecular weights of about 17.5 kD, and are produced from a precursor molecule with a molecular weight of about 31 kD.

Because IL-1 has pleiotropic biological activities many of which adversely affect the organism, it would be expected that the molecule must be tightly regulated if it is not to be injurious. Indeed, there are several reports of IL-1 inhibitors that regulate the action of IL-1. IL-1 inhibitory activity has been reported in monocyte conditioned medium, wherein the monocytes are grown on adherent immune complexes. Arena, W. P., et al., 1985, *Journal of Immun.,* 134:3868. Additionally, an inhibitor has been reported to be present urine. Seckinger, P., et al., 1987, *Journal of Immun.,* 139:1546. Lastly, a protein inhibitor, purified and cloned, that has interleukin-1 receptor antagonist activity has been reported. Hannum, et at., 1990, *Nature,* 343:336, and Eisenberg, S., et al., 1990, *Nature,* 343:341.

It is thought that the IL-1 inhibitor present in urine, and which has been partially purified and characterized by Seckinger, P. et al., supra and Seckinger, P., et al., 1987, *Journal of Immun.,* 139:1541 is similar, if not identical to the cloned IL-1 receptor antagonist reported by Eisenberg, S., et al., supra; and Carter, D., et (1990), Nature, 344:633.

It is thus becoming apparent that aside from their normal biological functions, which have not been fully elucidated, cytokines are pathologically associated with systemic changes arising from infection and tissue injury. No doubt cytokines will be found to play a role in diseases other than those mentioned above. Nevertheless, the importance of cytokines in disease, particularly sepsis, is readily apparent when the extent of the disease is considered. In the United States alone nosocomial bacteremia develops in about 194,000 patients, and of these about 75,000 die. Maki, D. G., 1981, *Nosocomiad Infect., (Dikson, R. E., Ed.), page* 183, Yrke Medical Books, U.S.A.. Most of these deaths are attributable to six major gram-negative bacilli, and these are *Pseudomonas aeruginosa, Escherichia coli*, Proteus, Klebsiella, Enterobacter and Serratia. The current treatment for bacteremia is the administration of antibiotics which, unfortunately, have limited effectiveness. Thus, it will be appreciated that there is an ongoing clinical need for medicaments that can be used by the physician to regulate the affects of cytokine production.

SUMMARY OF THE INVENTION

One aspect of the invention described herein consists of a class of protein inhibitors of cytokine activity that have applications for the therapeutic or prophylactic treatment of disease, preferably diseases involving IL-1. Hereinafter the inhibitor may alternatively be referred to as an inhibitor of cytokine activity, cytokine inhibitor, or IL- 1 cytokine inhibitor. By way of example, the activity of the inhibitor is demonstrated against IL-1 activity, without intending to suggest that the spectrum of activity of the inhibitor be so restricted. It is to be anticipated that by interfering with IL-1 activity that the inhibitor would additionally be interfering with the activity of other cytokines. Thus, in this sense the cytokine inhibitor described herein is an inhibitor of cytokine activity generally, and is the reason why it is alternatively referred to as IL-1 cytokine inhibitor.

A second aspect of the invention is the description of a protein inhibitor of cytokine activity that is an altered form of an IL-1 receptor antagonist.

A third aspect of the invention is the description of a cDNA sequence that encodes a protein inhibitor of cytokine activity.

A fourth aspect of the invention is the description of a cDNA sequence that encodes a protein inhibitor of cytokine activity that has a 5' coding region that is distinguishable from a prior art IL-1 receptor antagonist A fifth aspect of the invention is a description of methods whereby an inhibitor of cytokine activity is used to beneficially treat patients, either prophylactically or therapeutically, that suffer from a variety of immunologically responsive diseases including sepsis.

A further aspect of the invention is a description of diagnostic procedures for detecting disease as a function of cytokine inhibitor activity.

BRIEF DESCRIPTION OF THE DRAWINGS

FIG. 1 shows the partial sequence of MAD 15.

FIG. 2 shows the cDNA sequence of a variant IL-1 cytokine inhibitor and the predicted protein sequence.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference.

In its primary aspect, the present invention concerns the isolation and identification of a particular factor, hereinafter referred to as cytokine inhibitor factor, or simply, inhibitor, that inhibits the activity of IL-1. This inhibitor is characteristic of several cell types, including monocytes, fibroblasts, and various tumor cell lines but would be present in virtually all cell types that require an IL-1 inhibitor to counter balance the activity of IL-1. The cytokine inhibitor has been characterized with respect to certain of its molecular and chemical properties. Each of these will be discussed separately below.

Before discussing the subject invention cytokine inhibitor, it is important to be aware that the inhibitor described herein consists of proteinaceous material having a defined chemical structure. However, the precise structure of the inhibitor depends on a number of factors, particularly chemical modifications known to occur to proteins. For example, since all proteins contain ionizable amino and carboxyl groups it is, of come, apparent that the inhibitor may be obtained in acidic or basic salt form, or in neutral form. It is further apparent, that the primary amino acid sequence may be augmented by derivatization using sugar molecules (glycosylation) or by other chemical defivatizations involving covalent, or ionic attachment to the inhibitor with, for example, lipiris, phosphate, acetyl groups and the like, often occurring through association with saccharides. These modifications may occur in vitro, or in vivo, the latter being performed by a host cell through post-translational processing systems. It will be understood that such modifications, regardless of how they occur, are intended to come within the definition of the cytokine inhibitor so long as the activity of the protein, as defined below, is not destroyed. It is to be expected, of course, that such modifications may quantitatively or qualitatively increase or decrease the biological activity of the molecule, and such chemically modified molecules are also intended to come within the scope of the invention.

As used herein, "chromatography" is defined to include application of a solution containing a mixture of compounds to an adsorbent, or other support material which is eluted, usually with a gradient or other sequential eluant. Material eluted from the support matrix is designated eluate. The sequential elution is most routinely performed by isolating the support matrix in a column and passing the eluting solution(s), which changes affinity for the support matrix, either stepwise or preferably by a gradient, through the matrix. It will be appreciated that encompassed within the definition "chromatography" is the positioning of the support matrix in a filter and the sequential administering of eluant through the filter, or in a batch-mode.

The phrase "hydrophobic interaction matrix" is defined to mean an adsorbent that is a hydrophobic solid such as polystyrene resin beads, rubber, silica-coated silica gel, or crosslinked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high salt eluant containing anions such as chloride ion which bind to the anion exchange matrix and displace the adsorbed material.

By the phrase "high salt concentration conditions" is meant an aqueous solution wherein an ionic substance is present to create conditions of high ionic strength. Ionic strength is defined as is generally understood in the art and can be calculated from the putative concentrations of the various ions placed in solution modified by their activity coefficient. High salt concentrations that are routinely employed are typified by solutions containing high concentrations of ammonium surfate; however, other salts, such as sodium chloride, potassium chloride, sodium sulfate, sodium nitrate, or sodium phosphate may also be employed.

The definition of "affinity chromatography" is understood to be similar to that of Wilchek et al., 1984, *Methods in Enzymology*, 104:3. In its broadest intended definition, "affinity chromatography" is a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment.

As used herein the term "transformed" in describing host cell cultures denotes a cell that has been genetically engineered to produce a heterologous protein that possesses the activity of the native protein. Examples of transformed cells are described in the examples of this application. Bacteria are preferred microorganisms for producing the protein. Synthetic protein may also be made by suitable transformed yeast and mammalian host cells.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intrapefitoneal, with intravenous being preferred.

As used herein, the term "prophylactic or therapeutic" treatment refers to administration to the host of the cytokine inhibitor either before or after infection or cancer detection. If the cytokine inhibitor is administered prior to exposure to the infecting agent, the treatment is prophylactic (i.e., it protects the host against infection), whereas if administered after infection or initiation of cancer, the treatment is therapeutic (i.e., it combats the existing infection or cancer).

I. Identification of a cDNA Sequence that Encodes the Cytokine Inhibitor

A. General Cloning Techniques:

Establishing a cDNA library containing the cDNA sequence that encodes a truncated cytokine inhibitor, identification of the cDNA sequence, and subcloning and expressing the sequence makes use of numerous methods known to the skilled practitioner. A general description of the methods and materials used is presented here for the convenience of the reader. More specifically, construction of suitable vectors containing the desired cytokine coding sequence employs standard ligation and restriction methods wherein isolated vectors, DNA sequences, or synthesized oligonucleotides are cleaved, tailored, and religated in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. In the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15 to 25 minutes at 20° to 25° C. in 50 mM Tris pH 7.6, 50 mM NaCl, 6 mM $MgCl_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 μl volumes under the following standard conditions and temperatures: 20 mM Tris-Cl pH 7.5, 10 mM $MgCl_2$, 10 mM DTT, 33 μg/ml BSA, 10 mM-50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 μg/ml total DNA concentration. In blunt end ligations, the total DNA concentration of the ends is about 1 μM.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per μg of vector at 60° C. for about 1 hour. Nucleic acid fragments are recovered by extracting the preparation with phenol/chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the an. Miniprep DNA can be prepared from the transformants by the method of D. Ish-Howowicz et at., (1981 *Nucleic Acids Res.*, 9:2989) and analyzed by restfiction and/or sequenced by the dideoxy method of F. Sanger et al., 1977, *Proc. Natl. Acad. Sci,* (USA), 74:5463 as further described by Messing et al., 1981, *Nucleic Acids Res.,* 9:309, or by the method of Maxam et al., 1980, *Methods in Enzymology,* 65:499.

Host strains used in cloning in M13 consists of *E. coli* strains susceptible to phage infection, such as *E. coli* K12 strain DG8 are employed. The DG98 strain has been deposited with ATCC Jul. 13, 1984 and has accession number 1965.

Depending on the host cell used, transformation is done using standard techniques appropriate to such cells. The calcium treatment employing calcium chloride, as described by Cohen, S. N. et al., 1972, *Proc. Natl. Acad. Sci.* (USA) 69:2110, and modifications as described by Hanahan, D., 1983, *J. Mol. Biol.,* 166:557–580 are used for procaryotes or other cells which contain substantial cell wall barriers. Infection with *Agrobacterium tumefaciens (Shaw et al.,* 1983, *Gene* 23:315) is used for certain plant cells. Transformations into yeast are carried out according to the method of Van Solingen et al., 1977, *J. Bacteriol* 130:946 and Hsiao et al., 1979, *Proc. Natl. Acad. Sci.* (USA) 76:3829.

Several transfection techniques are available for mammalian cells without such cell walls. The calcium phosphate precipitation method of Graham and van der Eb, 1978, *Virology* 52:546 is one method. Transfection can be carded out using a modification (Wang et al., 1985, *Science* 2215:149) of the calcium phosphate co-precipitation technique. Another transfection technique involves the use of DEAE-dextran (Sompayrac, L. M. et al., 1981, *Proc. Natl. Acad. Sci. USA* 78:7575–7578). Alternatively, Lipofection refers to a transfection method which uses a lipid matrix to transport plasmid DNA into the host cell. The lipid matrix referred to as Lipofectin Reagent is available from BRL. Lipofectin Reagent comprises an aqueous solution (deionized and sterile filtered water) containing 1 mg/ml of lipid (DOTMA:DOPE, 50:50). This liposome-mediated transfection is carried out essentially as described by Felgner, P. L. et al. (1987, *Proc. Natl. Acad. Sci. U.S.A.* 84:7413). Lipofectin Reagent and DNA are separately diluted into serum free media so as to avoid gross aggregation which can occur when either material is too concentrated. For example, $0.5 \times 10^6$ cells are seeded onto a 60 mm tissue culture dish, and 1.5 ml of serum free media containing 1 to 20 µg of DNA and a second solution of 1.5 ml serum free media containing about 30 µg of Lipofectin are prepared. The diluted DNA and Lipofectin solutions are mixed and applied onto the cells. The transfection is inhibited by serum, so the cells are washed well with serum free media before adding the Lipofectin/DNA mixture.

Synthetic oligonucleotides are prepared by the triester method of Matteucci et al., 1981, *J. Am Chem. Soc.* 103:3185 or using commercially available automated oligonucleotide synthesizers. Kinasing of single strands prior to annealing or for labeling is achieved using an excess, e.g., approximately 10 units of polynucleotide kinase to 0.1 mmole substrate in the presence of 50 mM Tris, pH 7.6, 10 mM $MgCl_2$, 5 mM dithiothreitol, 1–2 mM ATP, 1.7 pmoles $^{32}$P-ATP (2.9 mCi/mmole), 0.1 mM spermidine, 0.1 mM EDTA.

A specific nucleic acid sequence may be cloned into a vector by using primers to amplify the sequence which contain restriction sites on their non-complementary ends according to the general methods as disclosed in U.S. Pat. Nos. 4,683,195 issued Jul. 28, 1987, 4,683,202 issued Jul. 28, 1987 and 4,800,159 issued Jan. 24, 1989 the latter of which is incorporated herein by reference in its entirety. A modification of this procedure involving the use of the heat stable Thermus aquaticus (Taq) DNA polymerase has been described and characterized in European Patent Publication No. 258017 published March 2, 1988 incorporated herein by reference in its entirety. Also useful is the Thermal Cycler instrument (Perkin-Elmer-Cetus) which has been described in European Patent Publication No. 236,069, published Sep. 9, 1987 also incorporated herein by reference in its entirety.

Generally, the nucleic acid sequence to be cloned is treated with one oligonucleotide primer for each strand and an extension product of each primer is synthesized which is complementary to each nucleic acid strand. An alternative to the use of plasmid DNAs encoding the lymphokines of interest as template for PCR is the use of RNA from any cell producing these lymphokines as template for PCR as described in U.S. Pat. No. 4,800,159. If RNA is the available starting material, the extension product synthesized from one primer when separated from its complement can serve as template for synthesized of the extension product of the other primer. As previously mentioned, each primer contains a restfiction site on its 5' end which is the same as or different from the restriction site on the other primer. After sufficient amplification has occurred the amplification products are treated with the appropriate restriction enzyme(s) to obtain cleaved products in a restriction digest. The desired fragment to be cloned is then isolated and ligated into the appropriate cloning vector.

For portions of vectors derived from cDNA or gertomit DNA which require sequence modifications, site-specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature which permits hybridization of an exact match, but at which the mismatches with the original strand are sufficient to prevent hybridization. Plaques which hybridize with the probe are then picked and cultured, and the DNA is recovered. Details of site specific mutation procedures are described below in specific examples.

In the constructions set forth below, correct ligations for plasmid construction are confirmed by first transforming *E. Coli* strain MM294, or other suitable host, with the ligation mixture. Successful transformants are selected by ampicillin, tetracycline or other antibiotic resistance or using other markers, depending on the mode of plasmid construction, as is understood in the art. Further screening of transformants is possible using the technique of colony hybridization essentially as described in Maniatis, T. et at. (supra pp. 312–328). Briefly, colonies are lifted onto nitrocellulose filters and sequentially placed on each of four Whatman filters each saturated with one of the following solutions: (1) in 10% SDS; (2) 0.5 M NaOH/1 M NaCl; (3) 1.5 M NaCl, 1.5 M Tfis pH 8.0; (4) 2 X SSC for approximately 5 min. each. After cell lysis and binding the DNA, filters were prehybridized for 0.5–1 hr. at 42° C. in hybridization buffer containing 30% formamide followed by hybridization for 1–2 hrs at 42° C. Filters were washed three times in 2 X SSC and 0.1% SDS until background was reduced.

Plasmids from the transformants are then prepared according to the method of Clewell et al., 1969, *Proc. Natl. Acad. Sci.* (USA) 62:1159, optionally following chloramphenicol amplification (Clewell, 1972, *J. Bacteriol* 110:667). The isolated DNA is analyzed by restriction and/or sequenced by the dideoxy method of Sanger et at., 1977, *Proc. Natl. Acad. Sci.* (USA) 74:5463 as further described by Messing et all., 1981, *Nucleic Acids Res.* 9:309, or by the method of Maxam et al., 1980, *Methods in Enzymology* 65:499.

The expression of DNA that encodes a cytokine inhibitor can be carried out in a wide variety of cell types. Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., 1977, *Nature* 198:1056), the tryptophan (trp)promoter system (Goeddel et al., 1980, *Nucleic Acids Res.* 8:4057) and the lambda derived $P_L$ promoter (Shimatake et at., 1981, *Nature* 292:128), and N-gene ribosome binding site, which has been made useful as a portable control cassette, U.S. Pat. No. 4,711,845, issued Dec. 8, 1987 and incorporated herein by reference in its entirety, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848 issued May 19, 1987 and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, 1983, *Meth. Enz.* 101:307; U.S. Pat. No. 4,803,164 incorporated herein by reference in its entirety), other plasmid vectors suitable for yeast expression are known (see, for example, Stinchcomb et al., 1979, *Nature* 282:39, Tschempe et al., 1980, *Gene* 10:157 and Clarke et al., 1983, *Meth. Enz.* 101:300). Control sequences for yeast vectors include promoters for the synthesis of glycolytic enzymes (Hess et al., 1968, *J. Adv. Enzyme. Req.* 7:149; Holland et al., 1978, *Biochemistry* 17:4900).

Additional promoters useful in yeast host microorganisms and known in the art include the promoter for 3-phosphoglycerate kinase (Hitzeman et at., 1980, *J. Biol. Chem.* 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra ).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., 1981, *J. Biol. Chem.* 256:1385) or the LEU2 gene obtained form YEp13 (Broach et all., 1978, *Gene* 8:121); however, any vector containing a yeast compatible promoter, origin of replication and other control sequences is suitable.

It is also, of course, possible to express genes encoding proteins in eucaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et at., 1978, *Nature*, 273:113) vital promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446, incorporated herein by reference in its entirety. A modification of this system is described in U.S. Pat. No. 4,601,978, incorporated herein by reference in its entirety. General aspects of mammalian cell host system transformations have been described by Axel in U.S. Pat. No. 4,399,216 issued Aug. 16, 1983. Also useful is gene amplification in eucaryotic cells as described by Ringold in U.S. Pat. No. 4,656,134, issued Apr. 7, 1987, incorporated herein by reference in its entirety. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequence compatible with plant cells such as the nopaline synthase promoter and polyadenylation signal sequences (Depicker et al., 1982, *J. Mol. Appl. Gen.*, 1:561) are available. Additionally, methods and vectors for transformation of plant cells have been disclosed in PCT Publication No. WO 85/04899, published Nov. 7, 1985, and incorporated herein by reference in its entirety.

Host strains used in cloning and expression herein are as follows:

For cloning and sequencing, and for expression of construction under control of most bacterial promoters, *E. coli* strain MM294 obtained from *E. coli* Genetic Stock Center GCSC #6135, was used as the host. For expression under control of the $P_L N_{RBS}$ promoter, *E. coli* strain K12 MC1000 lambda lysogen, $N_7 N_{53} cI857 SusP_{80}$, a strain deposited with the American Type Culture Collection (ATCC 39531), may be used. *E. coli* DG116, which was deposited with the ATCC (ATCC 53606) on Apr. 7, 1987, may also be used.

For M13 phage recombinants, *E. coli* strains susceptible to phage infection, such as *E. coli* K12 strain DG98, are employed. The DG98 strain has been deposited with the ATCC (ATCC 39768) on Jul. 13, 1984.

Mammalian expression has been accomplished in COS-A2 cells and also can be accomplished in COS-7, and CV-1, hamster and murine cells. Insect cell-based expression can be in *Spodoptera frumperda*.

B. Establishment of a cDNA Library:

A full length cDNA sequence that encodes the cytokine inhibitor may be obtained using molecular biology techniques well known in the art, with the noted exceptions detailed below.

Several procedures are available for identifying the cytokine cDNA sequences. The preferred procedure is to generate a library using RNA isolated from adherent monocytes, but a library can be generated from virtually any source of biological material that expresses the cytokine inhibitor, indeed, cDNA libraries can even be purchased commercially. Monocytes are the preferred starting material because adherence to an appropriate surface induces the expression of the cytokine inhibitor.

An illustrative procedure for making a cDNA library containing the IL-1 cytokine inhibitor sequences consists of isolating total cytoplasmic RNA from a suitable starting material, and further isolating messenger RNA therefrom. The latter can be further fractionated into Poly (A+) messenger RNA, which in turn may be fractionated further still into Poly (A+) messenger KNA fractions containing cytokine inhibitor messenger RNA. The messenger RNA can then be reverse transcribed and cloned into a suitable vector to form the cDNA library.

More specifically, the starting material (i.e., tissue, cells) is washed with phosphate buffered saline, and a non-ionic detergent, such as ethylene oxide, polymer type (NP-40) is added in an amount to lyse the cellular, but not nuclear membranes, generally about 0.3%. Nuclei can then be removed by centrifugation at 1,000×g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25 M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA.

Alternatively, total cytoplasmic RNA may be isolated using the guanidine isothiocyanate-cesium chloride method as described by Chirgwin et al (1979) Biochemistry 18: 5294.

Polyadenylated (Poly A+) messenger RNA (mRNA) can be obtained from the total cytoplasmic RNA by chromatography on oligo (dT) cellulose (J. Aviv et at., 1972, *Proc. Natl, Acad. Sci.* 69:1408–1412). The RNA is dissolved in ETS (10 mM Tris, 1 mM EDTA, 0.5 % SDS, pH 7.5) at a concentration of 2 mg/ml. This solution is heated to 65° C. for 5 minutes, then quickly chilled to 4° C. After bringing the RNA solution to room temperature, it is adjusted to 0.4 M NaCl and slowly passed through an oligo (dT) cellulose column previously equilibrated with binding buffer (500 mM NaCl, 10 mM Tris, 1 mM EDTA, pH 7.5) The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2 M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and AMV reverse transcriptase employing the method of H. Okayama et al., 1983, *Mol. Cell Biol.* 3:280, incorporated herein by reference.

Other methods of preparing cDNA libraries are, of come, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Ser. No. 564,224, fried Dec. 20, 1983, and assigned to the same assignee, incorporated herein by reference.

Using the partial amino acid sequence of a known IL-1 receptor antagonist inhibitor described by Hannum, et al., 1990, *Nature,* 343:336, and Eisenberg, S., et al., 1990, *Nature,* 343:341, and known codon redundancies thereto, several DNA oligonucleotide probes may be synthesized and used to screen the cDNA library.

A preferred method by which a cDNA clone that encodes the IL-1 cytokine inhibitor may be identified is to employ a cDNA library that is produced using RNA obtained from induced monocytes, and to detect individual clones that differentially hybridize to cDNA probes produced using RNA from induced and uninduced monocytes. Clones that preferentially hybridize to cDNA probes produced from induced but not uninduced monocyte RNA will contain cDNA that encodes the cytokine inhibitor of the instant invention.

cDNA inserts may be sequenced using known techniques. The preferred technique is to subclone the inserts into an appropriate vector, an exemplary vector being pGEM blue (Promega Biotec. Madison, Wis. Corp.), and sequence the double stranded DNA using the dideoxy chain termination method described by Sanger et. al., 1977, Proc. Natl. Acad. Sci. USA. 74:5463. Sequencing is conveniently performed using commercially available kits, preferably the Sequenase sequencing kit produced by United States Biochemical Co. Cleveland, Ohio, and using suitable primers, such as T7 and SP6 obtainable from Promega Biotec. Madison, Wis., and sequence specific primers.

1. Preferred Embodiment

The preferred procedure for constructing a cDNA library that contains a cDNA sequence that encodes the IL-1 cytokine inhibitor is to generate the library from RNA isolated from adherent monocytes. Briefly, the starting material consists of adherent monocytes. Monocytes may be obtained fresh from human volunteers, or from the American Red Cross. In both instances, the monocytes are isolated from whole blood initially in the form of a mononuclear cell fraction prepared by Ficoll-Hypaque sedimentation methods known in the art. Boyun, A., 1968, *Scandinavian J. of Clinical Lab. Invest.,* 21:77. The monocytes are then isolated from the mononuclear fraction by density fractionation using Pertoll. Ulmer, A. J., and Flad, D. H., 1979, *J. of*

*Immunological Methods*, 30:1. Alternatively, monocytes may be isolated by plating them onto plastic tissue culture dishes as described by Eierman, D. F., et al., 1989, *J. of Immunology*, 142:1970.

The monocytes are induced for expression of the IL-1 cytokine inhibitor by seeding the monocytes onto tissue culture plates or fibronectin coated tissue culture plates as generally described by Eierman, D. F., et al., 1989, *J. Immunol.*, 142:1970. In addition to fibronectin, a variety of other materials may be used to coat the tissue culture plates to effect monocyte adherence, and include collagen. Briefly, 100 mm tissue culture plates are coated with 100 µg/ml of human fibronectin in phosphate buffered saline (PBS) for 45 minutes at 37° C. Excess fibronectin is removed by washing the plates with PBS and the plates air dried before use. Monocytes are seeded onto the plates and are adherent to the tissue culture plates for at least the 30 minutes prior to the total RNA being extracted therefrom. The monocytes are cultured in RPMI 1640 media containing 20 µg/ml of gentamicin surfate at 37° C. in an atmosphere of 95% air/5 %$CO_2$. Generally, about $1-2 \times 10^7$ cells are seeded per 100 mm dish.

Next, adherent monocytes are lysed after removing the culture medium by adding 3.5 ml of a solution containing 4M guanidinium thiocyanate solution previously prepared by mixing 50 g of Fluka pure grade material with 0.5 g of sodium N-lauroylsarcosine (final concentration 0.5%), 2.5 ml of 1M sodium citrate, pH 7.0 (25 mM), and 0.7 ml of 2-mercaptoethanol (0.1M). The solution is made up to 100 ml with deionized water, and filtered to remove any insoluble material. The pH was adjusted to 7 with 1 M NaOH.

Next, the monocyte RNA is separated from the guanidinium thiocyanate homogenate by ultra centrifugation through a dense cushion of cesium chloride. Technical grade cesium chloride is made 5.7M and buffered with 0.1M EDTA, pH 7, or 25 mM sodium acetate or citrate, pH 5. The solution is sterilized with 0.2% diethyl pyrocarbonate, and filtered through a 0.45 µm Millipore filter. The monocyte RNA in the guanidinium thiocyanate is then separated from the guanidinium thiocyanate by ultracentrifugation through the cesium chloride cushion. The RNA pellets that form after the ultracentrifugation are redissolved if necessary by brief heating at 68° C. in a water bath, or by first extracting excess cesium chloride from the RNA pellets with ethanol and drying with nitrogen. RNA isolated in this manner may be used to prepare an appropriate cDNA library.

Total RNA isolated as described above may be used for construction of a cDNA library using those methods described by Watson and Jackson, 1985, *DNA Cloning*, 1:79, "A Practical Approach", (D. M. Glover, ed.), IRL Press, Oxford; and Huynh, et al., 1985, "Constructing and Screening Libraries in Lambda GT10 and Lambda GT11", *DNA Cloning*, 1:49, A Practical Approach, (D. M. Glover, ed.), IRL Press, Oxford. This method entails converting the RNA to double stranded cDNA using AMB reverse transcriptase and the Klenow fragment DNA polymerase 1, as is known in the art. EcoRI linkers were ligated to the double stranded cDNA fragments, size selected and packaged into lambda gT10 vector using a commercially available packaging extract, Gigapack (Stratagene, San Diego, Calif.). This library contained about $5.3 \times 10^6$ recombinants at a frequency of about $7 \times 10^7$ per µg of DNA.

From the library described above, a sub-library was derived by selecting 4,000 clones that do not hybridize to a $^{32}$P-labelled first-strand cDNA probe that was made using RNA obtained from uninduced monocytes.

The sub-library described above was screened by differential hybridization with $^{32}$P-labelled fast-strand cDNA probes prepared by reverse transcription of RNA isolated from monocytes that adhere for either 30 minutes or 4 hours, or from controlled non-adherent monocytes. Those plaques which exhibited hybridization with the cDNA probe made from adhered monocytes compared to non-adhered monocytes were selected, and rescreened with the probe. This resulted in the isolation of a partial 1107 base pair cDNA that encodes for a 1.6 kb mRNA. The clone was termed MAD 15, and partially sequenced (FIG. 1).

To isolate a full length DNA sequence that encodes the IL-1 cytokine inhibitor a second cDNA library was constructed and the sequence isolated therefrom, using as a probe MAD 15. cDNA was generated from RNA obtained from induced peripheral blood lymphocytes. Such procedures are well known in the art. The preferred procedure consists of inducing peripheral blood cells for three days with a calcium ionophore and mezerein. The preferred induction ionophore is A-23 187. The induction procedure is generally described in U.S. Pat. No. 4,376,821.

Leukocytes were induced with 100 ng/ml of mezerein and 0.25 ug/ml of A- 23187. The induction period was about 3 days, afterwhich Total RNA was isolated from induced peripheral blood lymphocytes using essentially the guanidinium thiocyanate-cesium chloride method outlined above, and from the total RNA fraction poly (A+) messenger RNA can be isolated by chromatography on oligo (dT) cellulose as described above.

Next, the first strand of the cDNA was obtained by reverse transcribing the mRNA as follows. 33 µg of the poly (A+) RNA was dispensed into a micro-centrifuge tube, and incubated for 5 minutes at 65° C., and then cooled on ice for 5 minutes. Next, to the RNA is added sequentially the following. 66 µl of 250 mM Tris-HCl, pH 8.3, 375 mM KCl, 15 mM of $MgCl_2$, 10.0 mM DTT; 9.0 µl RNA's in [40 U/µl]; 16.5 µl of 10 mM dNTP's; 35.0 µl of $p(dT)_{12-18}$ (100 pmole/µl); and 16.5 µl of MLV-reverse transcriptase (200 U/µl), and water to bring to a total volume of 330 µl.

To monitor the efficiency of first strand synthesis by alkaline agarose gel electrophoresis, a second robe is prepared that contains 2 µl [$\alpha^{32}$P] dCTP (10 µCi/µl), and 20 µl of the first strand reaction mixture prepared as described above.

Both tubes are incubated for 60 minutes at 37° C. followed by stopping the reactions by putting the robes on ice. Five µl of 0.5 M EDTA and 23 µl of water is added to the robe containing [$\alpha^{32}$P] dCTP. Both tubes are stored at $-20°$ C.

The second strand of the cDNA duplex is prepared as follows. 37.5 µl of the first strand mixture synthesized as described above is aliquoted into 8 separate robes, on ice. Also, 6.25 µl of the mix is pipetted into a 9th tube, on ice. Next, to each of the 8 tubes 262.5 µl of a second strand cocktail is added, and to the remaining, or control tube, 43.75 µl is added. The second strand cocktail consist of the following. 600.0 µl 5×SSB (5×SSB consists of 94 mM Tris-HCl, pH8.3, 453 mM KCl, 23.3 mM $MgCl_2$, 18.7 mM DTT) 1802.9 µl water, 56.3 µl 10 mM dNTP's, 12.5 µl [$\alpha^{32}$P] dCTP, 75.0 µl 6 mM β-AND, 75.0 µl DNA polymerase I (10 u/µl), and 3.4 µl of *E. coli* ligase (9 u/µl). The total volume of the reagents in the second strand cocktail is 2,625.0 µl. All 9 tubes are incubated for 2 hours at 16° C., after which to the 9th tube is added 5 µl of 0.5 M EDTA and 65 µl of water. The contents of this tube are stored at $-20°$ C. for subsequent alkaline agarose gel analysis.

Next, the contents of the 8 tubes are phenol extracted and twice ethanol precipitated, and the pellets combined in 128 µl of TE.

The cDNA prepared above is treated with Rnase H as follows. To 128 μl of cDNA is added the following: 128 μl 5×Rnase H buffer which consist of 100 mM Tris-HCL, pH 7.5, 100 mM KCl, 50 mM $MgCl_2$, 0.7 mM DTT, and 0.5 mM EDTA. Additionally, the tube contains 377.3 μl water, and 6.7 μl of Rnase H ( 1.9 u/μl). The total volume of the Rnase H reaction digest is 640 μl. The mixture is incubated at 37° C. for 20 minutes after which 5 μl of 0.5 M EDTA is added to terminate the reaction. Finally, the reaction mixture is phenol extracted, twice ethanol precipitated, and the pellet resuspended in 12 μl of TE.

The cDNA is fractionated and purified by neutral agarose gel electrophoresis. cDNAs of about 0.25–7.0 kilo bases in length were removed from the gels, glass bead purified, and resuspended in 107.5 μl of glass distilled water.

Next, the cDNA is C-tailed, and cloned into the vector pCDLSRα-296 [obtained from DNAX corporation, and described by Takebe et al (1988) Molecular and Cellular Biology, vol 8, No. 1, page 466; and in U.S. Pat. No. 4,695,542, which corresponds to Ser. No. 590,867] as follows. Prepare 10×terminal transferase buffer as follows: 13.8 g cacodylic acid is added to 3.0 g Tris-base in 60 ml of water. The solution is adjusted to pH 7.6 by slow addition of solid KOH, after which the volume is increased to 88 ml with water. Subsequently, the solution is chilled to 0° C., then 2 ml of 0.1 M DTT is added followed by the addition of 10 ml of 0.1 M $MnCl_2$ dropwise while the solution is being constantly stirred. To the 38.3 μl of 10×TDT buffer is added 5.7 μl of 1 mM dCTP, 0.6 μg of double stranded cDNA. An amount of water is added to bring the solution to a total volume of 380.5 μl. The solution is warmed to 37° C. for 15 minutes, and 360 units of TdT in about 3 μl is added. 60 μl aliquot are removed at various times and combined with 468 μl of 1 mM EDTA. Each aliquot is then combined with previously G-tailed vector in a suitable amount of annealing buffer, and transformed into an appropriate host. The C-tailed stock that produces the greatest number of transformants is used for the large scale transformation.

The cDNAs are cloned into the plasmid vector, pCDL-SRα296. The vector is prepared as follows. 200 μg of the plasmid is digested with 700 units Pst I in 500 μl total volume, for 60 minutes at 37° C. The plasmid is then phenol extracted, and twice ethanol precipitated, and resuspended in 200 μl of distilled water. The concentration is determined by spectrophotometry. Next, about 136 μg of pCDL-SRα296, 112.6 pmole 3' ends, was G-tailed by combining it in a solution consisting of 30 μl of 10× TdT buffer, 30 μl [$^3$H] dGTP (approximately 70 pmole/μl), 5.5 μl of 1 mM dGTP and water to make a total volume of 297 μl. The tailing reaction is conducted for various times, and the procedure consists of removing 30 μl from the reaction tube and combining it with 359 μl of 17 mM EDTA, which is the 0 time point. Next, 360 units of terminal transferase in 3 μl is added to prewarmed reaction digest mixture, 15 minutes at 37° C., and 30 μl of the mixture removed at various time intervals and the reactions stopped by pipetting it into 359 μl of 17 mM EDTA. The amount of G-tailing is monitored by determining the incorporation of [$^3$H] dGTP, as is known in the art. To ensure that the pCDL-SRα296 vector is properly G-tailed and that it is not contaminated with untailed vector, a trial annealing and transformation of DH5α is conducted as is known in the art. The vector is stored at −20° C. and used to clone the above described C-tailed cDNA.

Briefly, cloning into pCDL-SRα296 consisted of combining 88 μl of C-tailed cDNA corresponding to each time point, 2 μl G-tailed vector, and 10 μl of 10× annealing buffer. The total volume was 100 μl. The 10×annealing buffer consisted of: 0.1 M Tris-HCL, pH 7.6, 1.0 M NaCl, 10 mM EDTA. The annealing reaction was conducted under standard conditions, and the mixture transformed into DH5 bacteria.

The cDNA library obtained above may be amplified using either procedures well known in the art, or a novel solid state amplification technique described as follows. The procedure consists of suspending bacterial transformants in low melting temperature agarose. This contrast with state of the an methods that plate the bacterial transformants on suitable culture dishes. The following materials and methods are utilized. 0.3% Seaprep agarose in LB media, maintained at 37° C. in a water bath. An appropriate amount of cDNA annealed to pCDL-SRα296 and transformed into DH5α to generate up to about $2.5 \times 10^6$ cfu/ml. To the appropriate amount of agarose is added ampicillin to make 50 μg/ml and approximately $1.25 \times 10^6$ cfu of bacterial transformants. 25 ml of this solution is poured into 50 ml conical robes (Falcon Corp. No. 2098). The tubes are placed in an ice water bath for 20–60 minutes, and incubated overnight at 37° C. To assess the titre of the transformant mixture, 100 μl is plated on LB-amps$^{50}$ plates.

The library may be stored by pelleting the cells in 500 ml centrifuge bottles at 8 K for 20 minutes at room temperature. The cell pellets are resuspended in a total volume of 100 ml of 12.5% glycerol in LB media. Aliquots of the suspension are stored at −70° C.

The library was screened for cDNAs that encode the IL-1 inhibitor using the partial cDNA, MAD 15 as a probe. MAD 15 was partially sequenced and the sequence is shown in FIG. 1.

$10^5$ colonies of the SR/α cDNA library were screened, and a single full length cDNA sequence was obtained. It is shown in FIG. 2, along with the putative protein sequence.

It is noteworthy that the cDNA sequence indicates that the inhibitor lacks a leader peptide when compared to a prior art inhibitor shown in WO89/11540. Thus, the instant inhibitor is primarily intracellular.

The IL-1 inhibitor may be expressed in a variety of systems as described above. Mammalian expression may be accomplished in COS-A2 cells or in COS-7, and CV-1, hamster and murine cells. Insect cell-based expression can be in *Spodoptera frugiperda*.

II. Purification of the Cytokine Inhibitor

A. General Methods:

The general scheme for isolation of the cytokine inhibitor and purification consists of releasing the molecule from the cytoplasm of appropriate cells, tissues or organs, followed by removing insoluble material and subjecting the soluble fraction to one or more chromatographic steps including anion and cation exchange chromatography. The preferred procedure is to initially subject the soluble fraction to anion exchange chromatography, followed by a second chromatographic step wherein the eluant from the anion exchanger is passed over a cation exchanger. The IL-1 cytokine inhibitor is eluted from the cation exchanger, and may be further purified by subjecting it to a third chromatographic step, such as hydrophobic or sizing chromatography, or a second anion exchange step. It is important to note that the order of the various chromatographies may be varied to effect optimal purification of the inhibitor.

More specifically, the cytokine inhibitor is prepared by releasing the molecule from the cytosol using any number of techniques including freeze thawing, sonication, mild detergent extraction, etc. This procedure is preferably carried out in a physiologically buffered solution containing one or more protease inhibitors. Moreover, to further inhibit protease activity, especially those proteases that rely on metal ions for activity, the extraction solution may contain metal ion chelators. The preferred extraction solution is a physiologically balanced salt solution containing the chelators ethyleneglycoltrichloroacetic acid (EGTA), or ethylenediaminetrichloroacetic acid (EDTA), plus the protease inhibitor phenylmethylsulfonylfluoride (PMSF). The metal ion chelator(s), as well as the protease inhibitor(s) are present at concentrations that effectively inhibit proteolysis, preferably about 5 mM and 100 μM, respectively. However, it will, of course, be appreciated by those skilled in the art that since the types and amounts of proteases vary depending on the starting material used to extract the cytokine inhibitor, the concentrations that the protease inhibitors or chelators are used at, if indeed used at all, will also vary.

The mixture containing the cytokine inhibitor is clarified by centrifugation, or in other ways to remove insoluble material from the aqueous cytosol fraction. If the cytosol fraction contains low amounts of the cytokine inhibitor can be concentrated by any one of several techniques well known to those skilled in the art, including high salt precipitation, such as, for example, with ammonium sulfate, or by ultra filtration. If the cytokine inhibitor is concentrated by precipitation, it is preferably subsequently resuspended in a suitable physiologically balanced salt solution containing protease inhibitor(s) and preferably about 0.1% of a non-ionic detergent, such as NP40. This solution is then prepared for ion exchange chromatography by dialyzing it against a compatibly buffered chromatographic solution, preferably containing millimolar phosphate, a metal ion chelator, a reducing agent, and a protease inhibitor.

The inhibitor dialyzate is then subjected to chromatographic purification consisting preferably of three steps. The first involves purification using an ion exchange chromatographic step compatible with the cytokine inhibitor extraction buffer. Since the preferred extraction buffer contains phosphate, the initial step is purification of the cytokine inhibitor by cation exchange chromatography. The second consists of ion exchange chromatography wherein the ion exchange matrix has the opposite ion binding capacity from that of the first ion exchanger employed.

Thus, the preferred purification scheme will consist of applying the phosphate solution containing the cytokine inhibitor to a cation exchanger, and eluting it therefrom, preferably using solutions which alter the pH or conductivity of the solution. More preferably, the cytokine inhibitor will be eluted by applying either a gradient or non-gradient salt solution, and most preferably will be eluted using a linear gradient of sodium chloride over the range of about 0–0.6 molar.

The preferred cation exchanger is a SP-cellulose cation exchanger. Such are commercially available from AMF Molecular Separations Division, Meridian, CT under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the cytokine inhibitor solution. The flow rate of the solution through the matrix will depend upon the size and geometry of the matfix used. It will be apparent to those skilled in the art, however, that care should be taken to avoid exceeding the unit capacity of the matrix with the cytokine inhibitor. If the capacity is exceeded, the cytokine inhibitor will not be totally retained and excess unretained inhibitor will be present in the effluent. The capacity of the matrix to retain the inhibitor can be monitored by assaying for inhibitor activity in the effluent using one of the assays described below.

Fractions containing the cytokine inhibitor are prepared for the second chromatographic step, that is, anion exchange chromatography. This consists of combining the fractions and adjusting the solution to a pH, and ionic strength compatible with anion exchange chromatography. A variety of anion exchangers are available, and depending on the type employed, the concentrations of these reagents will vary. DEAE-Sepharose or TSK-DEAE-5-PW may be employed. The general procedures for preparing and using these matrices are known to those skilled in the art. The preferred anion exchanger is TSK-DEAE-5-PW matrix. It is prepared by equilibrating it with a solution containing chloride ions at a pH of 8.5. More preferably, the solution will consist of Tris hydrochloride, pH 8.5 plus a reducing agent, a metal chelator, magnesium chloride, and a protease inhibitor. The concentrations of the metal chelator and protease inhibitor will vary and depend on how extensively the cytokine inhibitor is proteolyzed, and whether the proteases responsible are activated by metal ions. The concentration of monovalent cations, such as magnesium chloride and reducing agent can be determined empirically by monitoring inhibitor activity. Those concentrations which maintain the highest activity will be utilized. Generally, it is preferred that magnesium chloride and the reducing agent be present in the range of about 0.5–1 mM, and 0.1–1 mM, respectively.

The solution is then passed through the anion exchange matrix whereupon the cytokine inhibitor binds to the matrix. The preferred elution method consists of eluting the inhibitor using a linear salt gradient ranging from 0–0.6 M NaCl. The purity and activity of the inhibitor so obtained can be monitored as described below, and by sodium dodecyl sulfate polyacrylamide gel electrophoresis run under reducing conditions. Using these techniques it may be determined that the cytokine inhibitor has a molecular weight of about 15–20 kD.

The third chromatographic step consists of applying, after the anion exchange chromatography, either a second cation exchange step, or a hydrophobic interaction chromatographic step. The most preferred purification scheme utilizes a second cation exchange step. Application of either of these methods will generally increase the purity of the inhibitor to about 95%. If a cation exchange column is chosen, the materials and methods described above are similarly applicable here. Generally, this will consist of decreasing the salt concentration present in the anion column eluates and adjusting the pH to about 6.0. Here, as in the initial cation chromatographic step, several different types of cation exchange matrices can be employed; however, the preferred matfix is a SP-TSK column which is run under high pressure. If hydrophobic chromatography is selected, the ionic strength of the eluate from the anion exchanger should be increased to be compatible with hydrophobic interaction chromatography. The solution can then be passed through a hydrophobic interaction chromatographic matrix, and eluted using techniques known in the art, including decreasing the salt concentration, or eluting with a chaotropic agent. Either of the latter solutions may be used alone, or in combination.

A variety of hydrophobic interaction chromatographic matrixes may be utilized. Generally, the materials and methods for utilizing hydrophobic chromatography are described by S. Shaltie, 1984, *Methods in Enzymology*, 104:69. While it is apparent there are many hydrophobic chromatographic materials and methods that may be employed to purify the cytokine inhibitor, phenyl Sepharose is preferred, and it is further preferred that the chromatography be employed under high pressure. The general procedures for forming high pressure liquid chromatography involving a phenyl derivatized matrix are described by F. Regmaer, 1983, *Methods in Enzymology*, 91:137. The preferred phenyl derivatized matfix is available commercially from Bio-Rad Corporation, and is sold under the trade name Biogel TSK phenyl-5-PW.

It will be additionally appreciated by those skilled in the an that an alternative purification scheme may consist of an affinity chromatographic step. This may be achieved by binding the inhibitor to a suitable binding moiety such as anti-inhibitor antibodies. The inhibitor can then be released from the affinity matrix using an appropriate method, or if the matrix is composed of antibody, by pH or chaotropic agents.

In addition to the above described chromatographic methods, a further method, chromatofocusing may be employed. This technique is described in Pharmacia's "FPLC Ion Exchange and Chromatofocusing—Principles and Methods" (1985), and involves eluting proteins off a suitable chromatographic substrate as a function of pH.

Finally, it should be noted that while the preferred applications of the ion exchange materials described herein are in a column format, it will be appreciated that they may also be used in batch format as well.

B. Antibody Methods;

Because of the unique 5' end of the IL-1 inhibitor compared to prior art inhibitors, antibody that binds to the 5' end will facilitate purification of the instant inhibitor from a mixture of proteins containing other IL-1 inhibitors. The preferred antibody is monoclonal, but polyclonal antibody, and antibody fragments from monoclonal and polyclonal antibody that have binding activity is intended to come within the scope of the invention. The monoclonal may be of any appropriate species and may include mouse, rat, and human. The antibody may be a chimetic construct produced using recombinant techniques, homologous recombination, or a single chain antibody as is known in the art. Generally, any antibody construct that cross blocks the binding of an antibody that bindings to the IL-1 inhibitor is intended to come within the scope of the invention.

"Recombinant antibody" refers to antibody wherein one portion of each of the amino acid sequences of heavy and light chain is homologous to corresponding sequences in antibody derived from a particular species or belonging to a particular class, while the remaining segment of the chains is homologous to corresponding sequences in another. Most commonly, in a recombinant antibody the variable region of both light and heavy chain mirrors the variable regions of antibody derived from one species of mammals, while the constant regions are homologous to the sequences in antibody derived from another. However, this is not necessarily always the case; for example, Ward, et al., 1989, *Nature*, 941:544, have shown that variable chain alone can be expressed in bacteria with significant antigen binding activity. Also intended to come within the scope of "Recombinant antibody" is monoclonal Fab antibody produced using the techniques described by Huse, W. D. et al., 1989, *Science* 246:1275.

Two antibodies are "cross-blocking" or have a "shared epitope" when each antibody effectively blocks the binding of the other antibody in a binding inhibition assay. Thus, if antibodies A and B are cross-blocking, antibody A would not bind to its antigen when the antigen had been preincubated with antibody B, and antibody B would not bind to its antigen when the antigen had been preincubated with antibody A.

The procedure for generating monoclonal antibody to the IL-1 inhibitor is described below. The preferred fusion procedure for that is followed is described by Kohler & Milstein, 1975, *Nature*, 256:495, as modified by Fendly et al., in *Hybridoma*, 6:359 (1987).

Balb/c mice are immunized via a primary intraperitoneal immunization consisting of 40 μg of the inhibitor in complete Freunds adjuvant, followed by two subsequent intraperitoneal injections without complete Freunds adjuvant, consisting of 20 μg of inhibitor each. The first immunization consisting of 20 μg is administered about three weeks after the primary immunization, and the second 20 μg boost is administered about one week later. About five and one half weeks after the second 20 μg boost, a final immunization is conducted consisting of administering 10 μg F intravenously. Three days later spleens from immunized mice are removed, and the splenocytes fused to a murine myeloma cell line.

Next, mice are sacrificed and splenocytes teased from immunized spleens, and washed in serum free Dulbecco's Modified Eagles medium. Similarly, SP $^2$/OAg14 myeloma cells are washed, and combined with the splenocytes in a 5:1 ratio, spleen cells to myeloma cells. The cell mixture is pelleted, media removed and fusion affected by the addition of 1.0 ml of 40% (v/v) solution of polyethylene glycol 1500 by dropwise addition over 60 seconds at room temperature, followed by a 60 second incubation at 37° C. To the cell suspension with gentle agitation is added 9 ml of Dulbecco's Modified Eagles medium over 5 minutes. Cell clumps in the mixture are gently resuspended, the cells washed to remove any residual PEG and plated at about $2 \times 10^5$ cells/well in Dulbecco's Modified Eagles medium supplemented with 20% fetal calf serum. After 24 hours, the cells are fed a 2×solution of hypoxanthine and azaserine selection medium. The cells are plated in a total of 15.5 micro titers plates, which corresponds to 1488 wells. Subsequently, about 2.4 weeks later 684 wells will show good cell growth, and would be screened for antibody to the inhibitor using assays known in the art, and preferably an ELISA assay.

Hybridomas that secrete neutralizing antibody that bind to the IL-1 inhibitor can be identified by performing the IL-1 inhibitor assay described below and including the antibody to be tested in the reaction mixture. Neutralizing antibody would abrogate the inhibitory activity of the IL-1 inhibitor.

III. IL-1 Inhibitor Assay

Two assays can be employed for demonstrating the biological activity of the IL- 1 inhibitor, a thymocyte inhibition of proliferation assay and a dermal fibroblast inhibition of $PGE_2$ secretion assay.

Thymocytes respond to IL-1 when combined with phytohaemagglufinin by undergoing a proliferation response. The latter can be measured by $^3$H-thymidine incorporation or other methods known in the art Mosmann,T., 1983, *J. Immunol. Method*, 65:55. IL-1 inhibitor activity can be thus determined by measuring the inhibition of the proliferative response caused by IL-1, plus phytohaemagglutinin.

The second assay consist of measuring the inhibition of secretion by human dermat fibroblasts of $PGE_2$ caused by IL-1. It is known that after 6 hours of stimulation with IL-1, human dermat fibroblasts produce $PGE_2$ which can be readily measured by an ELISA assay.

Using either of the two assays described above, the instant IL-1 inhibitor can be identified and characterized.

Typically, the thymocyte assay would be conducted using about $1 \times 10^6$ thymocytes cultured in a suitable culture medium containing about 1 unit/ml of IL-1 and varying amounts of the material sought to be assayed for IL-1 inhibitory activity. Inhibition of proliferation can be measured as is known in the an using 3H-thymidine, or uptake of the tetrazolium salt MTT. Mosmann, above. Suitable controls are run including culturing thymocytes in the absence of the material being assayed.

Similarly, the inhibition of secretion of $PGE_2$ can be measured by plating in a suitable culture medium about $1\times10^5$ cells in a 96 well plate with 0.5 units/ml IL-1, and varying amounts of the material sought to be tested for IL-1 inhibitory activity. The presence of the inhibitor can be revealed by comparison to control cells incubated without inhibitory material that typically secrete about 50,000 pg/ml of $PGE_2$ after about 6 hours exposure to IL-1. $PGE_2$ can be assayed using an ELSIA or other assay as is known in the art. Eisenberg, 1990, *Nature*, 343:341.

IV. Distribution of the IL-1 Inhibitor

The presence of the IL-1 inhibitor of the instant invention in various tissues/cells was determined and compared to the prior an IL-1 inhibitor described in WO 89/11540. The procedure consisted of performing the polymerase chain reaction on tissue RNA. This procedure is well known in the an and is described in U.S. Pat. Nos. 4,683,202 and 4,683,195, both of which are hereby incorporated in their entirety. In general, the synthesis/amplification of DNA sequences by PCR involves an enzymatic chain reaction that produces, in exponential quantities, a specific DNA sequence, provided that the termini of the sequence are known in sufficient detail so that oligonucleotide primers can be synthesized which will hybridize to them, and that a portion of the sequence is available to initiate the chain reaction. One primer is complementary to the negative strand, and the other is complementary to the positive strand. As applied to the instant invention, the primers were specific 5' primers used in combination with a common 3' primer to identify unique products, or a 5' primer in combination with the same 3' primer to recognize a common sequence present in the open reading frame.

The primers used are shown Table 1 below. The sense and anti-sense primers, GM397 and GM368, respectively, were used to detect the instant IL-1 inhibitor mRNA. The presence of the inhibitor was compared to a prior an IL-1 inhibitor described in WO 89/11540 using sense and anti-sense primers GM398 and GM368, respectively. Of the primers, GM397 is specific for the instant IL-1 inhibitor, whereas GM398 and GM368 are homologous to sequences present in the prior an inhibitor. Using this method the following results were obtained.

TABLE 1

| | |
|---|---|
| GM368 | CAGGCCTCTAGAGTACTACTCGTCCTCCTGG |
| GM397 | CAGAAGACCTCCTGTCCTATGAGG |
| GM398 | GAATGGAAATCTGCAGAGGCCTCCGC |

The results are presented below in qualitative "+" and "−" fashion. This scoring system is not intended to indicate absolute amounts of IL-1 inhibitor mRNA; rather "+" and "−" indicates, considering the limits of the PCR method used, substantially more or less of the mRNA in the various materials tested.

| Cell Type | IL-1 Inhibitor | IL-1 Inhibitor (WO 89/11540) |
|---|---|---|
| Normal Human Retinal Pigmented Epithelial | + | − |
| Keratinocytes | + | − |
| IL-1 stimulated Breast Epithelium | + | − |
| Monocytes - Adherent to Fibronectin | +/− | + |
| Monocytes - Adherent to Collagen coated plates | + | + |
| Ovary | − | nd* |
| Endometrium | − | nd |

*nd, not determined

Using the PCR technique described above, it was additionally determined that mRNA that encodes the instant IL-1 inhibitor is present in 8 of 13 endometrial and ovarian rumor specimens. Since the mRNA is not present in substantial amounts in normal ovary or endometrium, but is present in tumor cells of similar origin, IL-1 inhibitor nucleotide sequences may be used to diagnose endometrial or ovarian tumors.

Further, only 1 of 18 normal stromal cell lines have, using PCR, detectable levels of IL-1 inhibitor mRNA.

V. Diagnostic Applications

Using the materials described herein, that is, antibody to the IL-1 inhibitor and nucleotide sequences that encode it, diagnostic methods may be employed to detect the presence of the inhibitor as an indicator of disease.

For example, the presence of the inhibitor may be detected and measured using antibody methods well known in the art. One method would involve a two site immunometric assay as described in U.S. Pat. No. 4,376,110.

Alternatively, because the IL-1 inhibitor DNA sequences disclosed herein are transcribed in various tumors and substantially less so, if at all, in normal cells, inhibitor nucleotide sequences, either DNA or RNA, would have diagnostic applications that would facilitate the detection of tumors or provide more accurate information regarding the tumorigenic state that a particular cell is in. One particular application would be to determine the number of copies of the inhibitor gene present per cell in various types of cancers, that is to say, whether the gene is amplified. Thus, the inhibitor nucleotide sequences disclosed herein can be used to measure the degree of over amplification, and diagnostic and prognostic correlations established.

The level of amplification can be determined following techniques generally known in the art. D. Slamon et al., 1987 *Science* 235:177; U.S. Pat. No. 4,542,092 and U.S. Pat. No. 4,699,877; R. Schimke, 1982 *Gene Amplification*, Cold Spring Harbor Laboratory. Additionally, polymerase chain reaction methods well known in the art, and alluded to above may also be employed.

VI. Therapeutic/Prophylactic Applications of IL-1 Inhibitor for the Treatment of Disease A. Sepsis:

One embodiment of the invention is the administration of an effective amount of the subject cytokine inhibitor to individuals that are at a high risk of developing sepsis, or that have developed sepsis. An example of the former category are patients about to undergo surgery. While the mode of administration is not particularly important, parenteral administration is preferred because of the rapid progression of sepsis, and thus, the need to have the inhibitor disseminate quickly throughout the body. Thus, the preferred mode of administration is to deliver an I.V. bolus slightly before, during, or after surgery. The dosage of the inhibitor will normally be determined by the prescribing physician. It is to be expected that the dosage will vary according to the age, weight and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the inhibitor will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the cytokine inhibitor will be formulated in such vehicles at a concentration of about 1–8 mg/ml to about 10 mg/ml.

B. Arthritis:

The immunosuppressive effects of the IL-1 inhibitor against rheumatoid arthritis may be determined in an experimental animal model system. The experimental model system is adjuvant induced arthritis in rats, and the protocol is described by J. Holoshitz, et at., 1983, *Science,* 219:56, or by B. Waksman and C. Wennersten, 1963, *Int. Arch. Allergy Appl. Immunol.,* 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The inhibitor would be administered in phosphate buffered solution (PBS) at a dose of about 1–5 mg/kg. The control would consist of administering PBS only.

The procedure for testing the effects of the IL-1 inhibitor would consist of intradermally injecting killed Mycobacterium tuberculosis in CFA followed by immediately administering the inhibitor and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the inhibitor would have a dramatic affect on the swelling of the joints as measured by a decrease of the arthritis score.

Although any similar or equivalent methods and materials may be employed in the practice or testing of the present invention, the preferred methods and materials are now described. The following examples are illustrative of this invention. They are not intended to be limiting upon the scope thereof.

The present invention has been described with reference to specific embodiments. However, this application is intended to cover those changes and substitutions which may be made by those skilled in the art without departing from the spirit and the scope of the appended claims.

We claim:

1. A protein comprising the amino acid sequence shown in FIG. 2, wherein said protein is isolated and essentially pure.

* * * * *